(12) United States Patent
Nicolini

(10) Patent No.: US 9,220,823 B2
(45) Date of Patent: *Dec. 29, 2015

(54) PRESSURE CONTROL APPARATUS

(71) Applicant: Smith & Nephew PLC, London (GB)

(72) Inventor: Derek Nicolini, Brough (GB)

(73) Assignee: SMITH & NEPHEW PLC, London (GB)

(*) Notice: Subject to any disclaimer, the term of this patent is extended or adjusted under 35 U.S.C. 154(b) by 11 days.

This patent is subject to a terminal disclaimer.

(21) Appl. No.: 14/256,658

(22) Filed: Apr. 18, 2014

(65) Prior Publication Data

US 2014/0316356 A1 Oct. 23, 2014

Related U.S. Application Data

(63) Continuation of application No. 13/824,982, filed as application No. PCT/GB2011/051745 on Sep. 16, 2011, now Pat. No. 8,734,425.

(30) Foreign Application Priority Data

Sep. 20, 2010 (GB) .................................. 1015656.0

(51) Int. Cl.
*A61M 1/00* (2006.01)
*A61F 13/00* (2006.01)
*A61M 5/168* (2006.01)

(52) U.S. Cl.
CPC ........ *A61M 1/0088* (2013.01); *A61F 13/00068* (2013.01); *A61M 1/0025* (2014.02);
(Continued)

(58) Field of Classification Search
CPC ............ A61M 1/0023; A61M 1/0025; A61M 1/0031; A61M 1/0037; A61M 1/0088; A61M 2205/15; A61M 2205/46831; A61M 2205/18; A61M 2205/3344; A61M 2205/8212
See application file for complete search history.

(56) References Cited

U.S. PATENT DOCUMENTS 3,972,328 A 8/1976 Chen
4,062,012 A 12/1977 Colbert et al.
(Continued)

FOREIGN PATENT DOCUMENTS

CN 101385887 A 3/2009
EP 1 476 217 11/2004
(Continued)

OTHER PUBLICATIONS

U.S. Appl. No. 61/828,604, filed May 29, 2013, Collinson et al.
(Continued)

*Primary Examiner* — Philip R Wiest
*Assistant Examiner* — Benjamin Klein
(74) *Attorney, Agent, or Firm* — Knobbe, Martens, Olson & Bear LLP

(57) ABSTRACT

Methods and apparatuses are disclosed for applying negative pressure to a wound site. In some embodiments, the apparatus comprises a source of negative pressure, a processing element, and a memory comprising instructions configured to, when executed on the processing element, cause the apparatus to attempt to generate, via the source of negative pressure, a desired negative pressure at the wound site. If the desired negative pressure has not been generated after a first predetermined period of time, the instructions cause the apparatus to: deactivate the source of negative pressure for a second predetermined period of time, and subsequently attempt to generate the desired negative pressure at the wound site.

20 Claims, 4 Drawing Sheets

(52) U.S. Cl.
CPC ........... *A61M1/0031* (2013.01); *A61M 1/0035* (2014.02); *A61M 1/0037* (2013.01); *A61F 2013/00174* (2013.01); *A61M 5/16831* (2013.01); *A61M 2205/15* (2013.01); *A61M 2205/18* (2013.01); *A61M 2205/3344* (2013.01); *A61M 2205/8212* (2013.01)

(56) References Cited

U.S. PATENT DOCUMENTS

| | | |
|---|---|---|
| 4,643,641 A | 2/1987 | Clausen et al. |
| 4,969,880 A | 11/1990 | Zamierowski |
| 5,127,388 A | 7/1992 | Cicalese et al. |
| 5,238,732 A | 8/1993 | Krishnan |
| 5,449,347 A | 9/1995 | Preen et al. |
| 5,549,584 A | 8/1996 | Gross |
| 5,616,121 A | 4/1997 | McKay |
| 5,676,525 A | 10/1997 | Berner et al. |
| 5,759,570 A | 6/1998 | Arnold |
| 6,071,267 A | 6/2000 | Zamierowski |
| 6,162,194 A | 12/2000 | Shipp |
| 6,626,891 B2 | 9/2003 | Ohmstede |
| 6,673,036 B1 | 1/2004 | Britto |
| 6,685,681 B2 | 2/2004 | Lockwood et al. |
| 6,752,794 B2 | 6/2004 | Lockwood et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,022,113 B2 | 4/2006 | Lockwood et al. |
| 7,108,683 B2 | 9/2006 | Zamierowski |
| 7,361,184 B2 | 4/2008 | Joshi |
| 7,381,859 B2 | 6/2008 | Hunt et al. |
| 7,524,315 B2 | 4/2009 | Blott et al. |
| 7,569,742 B2 | 8/2009 | Haggstrom et al. |
| 7,615,036 B2 | 11/2009 | Joshi et al. |
| 7,625,362 B2 | 12/2009 | Boehringer |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,964,766 B2 | 6/2011 | Blott et al. |
| 8,062,272 B2 | 11/2011 | Weston |
| 8,062,331 B2 | 11/2011 | Zamierowski |
| 8,080,702 B2 | 12/2011 | Blott et al. |
| 8,105,295 B2 | 1/2012 | Blott et al. |
| 8,118,794 B2 | 2/2012 | Weston et al. |
| 8,152,785 B2 | 4/2012 | Vitaris |
| 8,162,907 B2 | 4/2012 | Heagle |
| 8,207,392 B2 | 6/2012 | Haggstrom et al. |
| 8,241,261 B2 | 8/2012 | Randolph et al. |
| 8,282,611 B2 | 10/2012 | Weston |
| 8,303,552 B2 | 11/2012 | Weston |
| 8,323,264 B2 | 12/2012 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| D679,819 S | 4/2013 | Peron |
| D679,820 S | 4/2013 | Peron |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,628,505 B2 | 1/2014 | Weston |
| 8,641,691 B2 | 2/2014 | Fink |
| 8,715,256 B2 | 5/2014 | Greener |
| 8,734,425 B2 * | 5/2014 | Nicolini ........................ 604/543 |
| 8,808,274 B2 | 8/2014 | Hartwell |
| 8,834,451 B2 | 9/2014 | Blott et al. |
| 8,945,074 B2 | 2/2015 | Buan et al. |
| 2002/0026946 A1 | 3/2002 | McKay |
| 2002/0171553 A1 | 11/2002 | Omry et al. |
| 2002/0198504 A1 | 12/2002 | Risk et al. |
| 2003/0040687 A1 | 2/2003 | Boynton et al. |
| 2004/0118460 A1 | 6/2004 | Stinson |
| 2005/0251117 A1 | 11/2005 | Anderson et al. |
| 2005/0267402 A1 | 12/2005 | Stewart et al. |
| 2006/0009744 A1 | 1/2006 | Erdman et al. |
| 2006/0083623 A1 | 4/2006 | Higgins et al. |
| 2006/0122558 A1 | 6/2006 | Sherman et al. |
| 2006/0282174 A1 | 12/2006 | Haines |
| 2006/0282175 A1 | 12/2006 | Haines et al. |
| 2006/0287632 A1 | 12/2006 | Sarangapani |
| 2007/0016152 A1 | 1/2007 | Karpowicz et al. |
| 2007/0032762 A1 | 2/2007 | Vogel |
| 2007/0055209 A1 | 3/2007 | Patel et al. |
| 2007/0113849 A1 | 5/2007 | Matthews et al. |
| 2007/0219532 A1 | 9/2007 | Karpowicz et al. |
| 2007/0225663 A1 | 9/2007 | Watt et al. |
| 2007/0260226 A1 | 11/2007 | Jaeb et al. |
| 2008/0200857 A1 | 8/2008 | Lawhorn |
| 2008/0281281 A1 | 11/2008 | Meyer et al. |
| 2008/0306456 A1 | 12/2008 | Riesinger |
| 2009/0012441 A1 | 1/2009 | Mulligan |
| 2009/0030402 A1 * | 1/2009 | Adahan ........................ 604/540 |
| 2009/0123513 A1 | 5/2009 | Greener |
| 2009/0125004 A1 | 5/2009 | Shen et al. |
| 2009/0149821 A1 | 6/2009 | Scherson et al. |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0270833 A1 | 10/2009 | DeBelser et al. |
| 2009/0292264 A1 | 11/2009 | Hudspeth et al. |
| 2009/0299251 A1 | 12/2009 | Buan |
| 2009/0299306 A1 | 12/2009 | Buan |
| 2010/0042059 A1 | 2/2010 | Pratt et al. |
| 2010/0125258 A1 | 5/2010 | Coulthard et al. |
| 2010/0126484 A1 | 5/2010 | Skell et al. |
| 2010/0160880 A1 | 6/2010 | Weston |
| 2010/0207768 A1 | 8/2010 | Pidgeon |
| 2010/0211030 A1 | 8/2010 | Turner et al. |
| 2010/0244780 A1 | 9/2010 | Turner |
| 2010/0268198 A1 | 10/2010 | Buan et al. |
| 2010/0305526 A1 | 12/2010 | Robinson et al. |
| 2010/0324510 A1 | 12/2010 | Andresen et al. |
| 2011/0004172 A1 | 1/2011 | Eckstein et al. |
| 2011/0009838 A1 | 1/2011 | Greener |
| 2011/0028918 A1 | 2/2011 | Hartwell |
| 2011/0054421 A1 | 3/2011 | Hartwell |
| 2011/0054423 A1 | 3/2011 | Blott et al. |
| 2011/0060284 A1 | 3/2011 | Harr |
| 2011/0077605 A1 | 3/2011 | Karpowicz et al. |
| 2011/0098600 A1 | 4/2011 | Matsumura et al. |
| 2011/0118683 A1 | 5/2011 | Weston |
| 2011/0202220 A1 | 8/2011 | Seta et al. |
| 2011/0224631 A1 | 9/2011 | Simmons |
| 2011/0257572 A1 | 10/2011 | Locke et al. |
| 2011/0282309 A1 | 11/2011 | Adie et al. |
| 2012/0041399 A1 | 2/2012 | Blott et al. |
| 2012/0130325 A1 | 5/2012 | Blott et al. |
| 2012/0136325 A1 | 5/2012 | Allen et al. |
| 2012/0165764 A1 | 6/2012 | Allen et al. |
| 2012/0259299 A1 | 10/2012 | Ryu et al. |
| 2012/0271256 A1 | 10/2012 | Locke et al. |
| 2013/0085462 A1 | 4/2013 | Nip et al. |
| 2013/0110058 A1 | 5/2013 | Adie et al. |
| 2013/0116635 A1 | 5/2013 | Fleischmann |
| 2013/0138054 A1 | 5/2013 | Fleischmann |
| 2013/0138060 A1 | 5/2013 | Haqqstrom et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0267917 A1 | 10/2013 | Pan et al. |
| 2013/0267920 A1 | 10/2013 | Nicolini |

(56) References Cited

U.S. PATENT DOCUMENTS

| | | | |
|---|---|---|---|
| 2013/0274688 A1 | 10/2013 | Weston | |
| 2013/0331822 A1 | 12/2013 | Patel et al. | |
| 2013/0338613 A1 | 12/2013 | Haggstrom et al. | |
| 2014/0114268 A1 | 4/2014 | Auguste et al. | |
| 2014/0163490 A1 | 6/2014 | Locke et al. | |
| 2014/0228791 A1 | 8/2014 | Hartwell | |
| 2014/0249493 A1 | 9/2014 | Hartwell | |
| 2014/0276487 A1 | 9/2014 | Locke et al. | |
| 2014/0316359 A1 | 10/2014 | Collinson et al. | |
| 2015/0025482 A1 | 1/2015 | Begin et al. | |
| 2015/0032035 A1 | 1/2015 | Banwell et al. | |
| 2015/0051560 A1 | 2/2015 | Askem | |

FOREIGN PATENT DOCUMENTS

| | | |
|---|---|---|
| EP | 2 462 908 | 6/2012 |
| EP | 2 544 642 | 1/2015 |
| EP | 2 648 668 | 1/2015 |
| EP | 2 830 555 | 2/2015 |
| EP | 2 836 711 | 2/2015 |
| FR | 1163907 | 10/1958 |
| JP | 2001-241382 | 9/2001 |
| JP | 2000-105011 | 10/2001 |
| JP | 2001-286807 | 10/2001 |
| JP | 2010-185458 | 5/2010 |
| WO | WO 94/21312 | 9/1994 |
| WO | WO 98/19068 | 5/1998 |
| WO | WO 00/49968 | 8/2000 |
| WO | WO 00/56378 | 9/2000 |
| WO | WO 03/057307 | 7/2003 |
| WO | WO 2005/123170 | 12/2005 |
| WO | WO 2006/046060 | 5/2006 |
| WO | WO 2006/052839 | 5/2006 |
| WO | WO 2006/117207 | 11/2006 |
| WO | WO 2007/019038 | 2/2007 |
| WO | WO 2007/087811 | 8/2007 |
| WO | WO 2008/048481 | 4/2008 |
| WO | WO 2008/049029 | 4/2008 |
| WO | WO 2008/100440 | 8/2008 |
| WO | WO 2008/135997 | 11/2008 |
| WO | WO 2009/019415 | 2/2009 |
| WO | WO 2009/047524 | 4/2009 |
| WO | WO 2009/066104 | 5/2009 |
| WO | WO 2009/089390 | 7/2009 |
| WO | WO 2009/124100 | 10/2009 |
| WO | WO 2009/158128 | 12/2009 |
| WO | WO 2010/039481 | 4/2010 |
| WO | WO 2010/051418 | 5/2010 |
| WO | WO 2010/093753 | 8/2010 |
| WO | WO 2010/126444 | 11/2010 |
| WO | WO 2010/142959 | 12/2010 |
| WO | WO 2010/147533 | 12/2010 |
| WO | WO 2011/087871 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/131237 | 10/2012 |
| WO | WO 2012/140378 | 10/2012 |
| WO | WO 2012/143665 | 10/2012 |
| WO | WO 2013/010907 | 1/2013 |
| WO | WO 2013/064852 | 5/2013 |
| WO | WO 2013/083800 | 6/2013 |
| WO | WO 2013/136181 | 9/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |

OTHER PUBLICATIONS

U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
Japanese First Office Action, re JP Application No. 2013-528768, dated Jul. 27, 2015, in 10 pages.
Kendall ULTEC Hydrocolloid Dressing (4"x4"), product ordering page, web page downloaded Jul. 13, 2014.
Protz, Kerstin: "Modern Wundauflagen unterstutzen Heilungsprozess", Wundversorgung: Indikation und Anwendung, Geriatrie Journal Apr. 2005, pp. 3333-3339, with translation.
International Preliminary Report on Patentability issued on Mar. 26, 2013 in International Application No. PCT/GB2011/051745 in 7 pages.
International Search Report for PCT Application No. PCT/GB2011/051745, mailed Feb. 2, 2012 in 4 pages.
International Search Report and Written Opinion re PCT/IB2011/002943, dated Jan. 28, 2013 in 26 pages.
Chinese Office Action for corresponding Chinese application No. 201180055731.0, issued Sep. 1, 2015, in 6 pages.

* cited by examiner

PRESSURE CONTROL APPARATUS

CROSS-REFERENCE TO RELATED APPLICATIONS

This application is a continuation of U.S. patent application Ser. No. 13/824,982, filed on Jun. 26, 2013 and issued as U.S. Pat. No. 8,734,425, which is a U.S. National Phase application under 35 U.S.C. §371 of International Application PCT/GB2011/051745, filed Sep. 16, 2011, which claims priority to Great Britain Patent Application No. 1015656.0, filed Sep. 20, 2010. The disclosures of these prior applications are incorporated by reference in their entireties.

BACKGROUND OF THE DISCLOSURE

1. Field of the Disclosure

The present invention relates to a method and apparatus for applying a negative pressure. In particular, but not exclusively, the present invention relates to the application of a negative pressure to a wound site in the application of topical negative pressure at the wound site.

2. Background

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy (sometimes referred to as Vacuum Assisted Closure or negative pressure wound therapy) assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, which is incorporated herein by reference, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, which is incorporated herein by reference, apparatus, a wound dressing and a method for cleansing a wound using aspiration, irrigation and cleansing are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

However, this portable apparatus is still relatively bulky, and may require monitoring of the patient by a trained caregiver. Furthermore, such portable therapy units commonly have reduced capacity to deal with fluid flow rates into a wound cavity caused by leaks. This leads to a greater number of alarms being raised due to an inability to maintain the desired negative pressure at the wound site in the presence of leaks.

Another problem associated with portable apparatus is that on occasion an onboard power source such as a battery pack is used rather than a continuous connection to a power source such as a mains power source. It will be appreciated that such a battery pack has only a limited power resource and therefore TNP therapy can on occasion be halted prior to a desired moment in time because of power failure.

Another problem associated with therapy units which can be utilised by a patient alone without the need for skilled technical assistants is that from time to time warning lights or warning alarms may be initiated when a desired therapy can not be maintained or initiated. This can be distressing for a patient who may not understand the meaning of the cues.

A still further problem associated with the apparatus used to provide TNP therapy is that from time to time a motor associated with a pump which generates a negative pressure will start up or stop. The change in volume coming from the therapy unit can be a cause of concern to a patient.

SUMMARY OF SOME EXEMPLIFYING EMBODIMENTS

It is an aim of certain embodiments of the present invention to at least partly mitigate one or more of the above-mentioned problems.

It is an aim of certain embodiments of the present invention to provide a method for controlling the provision of a desired negative pressure at a wound site to aid in wound closure and healing.

It is an aim of certain embodiments of the present invention to provide a pressure control apparatus that avoids the generation of unnecessary alarms in the presence of transient leaks.

It is an aim of certain embodiments of the present invention to provide a pressure control apparatus that helps extend battery power lifetime.

It is an aim of certain embodiments of the present invention to provide a pressure control apparatus that reduces a number of pump motor start-up or power down operations.

According to a first aspect of the present invention there is provided apparatus for dressing a wound for the application of topical negative pressure at a wound site, comprising:
 a source of negative pressure;
 a processing element;

a memory comprising instructions configured to, when executed on the processor, cause the apparatus to perform the steps of:
  via the source of negative pressure, attempting to generate a desired negative pressure at the wound site;
  if the desired negative pressure has not been generated after a first predetermined period of time, deactivating the source of negative pressure for a second predetermined period of time; and
  subsequently attempting to generate the desired negative pressure at the wound site.

According to a second aspect of the present invention there is provided a method of applying topical negative pressure (TNP) at a wound site, comprising the steps of:
  via a source of negative pressure, attempting to generate a desired negative pressure at the wound site;
  if the desired negative pressure has not been generated after a first predetermined period of time, deactivating the source of negative pressure for a second predetermined period of time; and
  subsequently attempting to generate the desired negative pressure at the wound site.

According to a third aspect of the present invention there is provided an apparatus for applying negative pressure to a wound, comprising:
  a source of negative pressure coupled to a dressing; and
  a controller configured to:
    activate the source of negative pressure to generate a first desired negative pressure under the dressing;
    if, upon an expiration of a first time interval, a negative pressure under the dressing has not reached the first desired negative pressure, deactivate the source of negative pressure for a second time interval; and
    upon expiration of the second time interval, activate the source of negative pressure to generate the first desired negative pressure under the dressing.

In some embodiments, the controller is further configured to: deactivate the source of negative pressure when the first desired negative pressure has not been generated under the dressing after activating the source of negative pressure for a first number of times exceeding a first threshold.

In some embodiments, the controller is further configured to: when the first number of times exceeds the first threshold, deactivate the source of negative pressure for a third time interval.

In some embodiments, the apparatus further comprises: a switch configured to signal to the controller to activate or deactivate the source of negative pressure; and the controller is further configured to, upon expiration of the third time interval or upon receiving a signal to activate the source of negative pressure from the switch, activate the source of negative pressure to generate the first desired negative pressure under the dressing.

In some embodiments, the apparatus further comprises: an indicator, wherein the controller is further configured to activate the indicator when the first number of times exceeds the first threshold.

In some embodiments, the controller is further configured to: deactivate the indicator upon expiration of the third time interval or receiving a signal to activate the source of negative pressure from the switch.

In some embodiments, the indicator indicates a leak in the seal.

In some embodiments, the controller is further configured to:
  when the negative pressure under the dressing has reached the first desired negative pressure, deactivate the source of negative pressure and monitor negative pressure under the dressing; and
  if the negative pressure under the dressing drops below a negative pressure threshold, activate the source of negative pressure to generate a second desired negative pressure under the dressing.

In some embodiments, the first and second desired negative pressure are the same.

In some embodiments, the second desired negative pressure is less than the first desired negative pressure.

In some embodiments, the controller is further configured: to deactivate the source of negative pressure if the negative pressure under the dressing has reached the second desired negative pressure or if the negative pressure under the dressing has not reached the second desired negative pressure upon expiration of a fourth time interval.

In some embodiments, if the negative pressure under the dressing has not reached the second desired negative pressure upon expiration of the fourth time interval, the controller is further configured to, upon expiration of the second time interval, activate the source of the negative pressure to generate the first desired negative pressure under the dressing.

In some embodiments, the controller is further configured to: activate the source of the negative pressure to generate the first desired negative pressure under the dressing if the controller has activated the source of negative pressure to reach the second desired negative pressure for a second number of times less than a second threshold.

In some embodiments, the controller is further configured to:
  deactivate the source of negative pressure if the controller has activated the source of negative pressure to reach the second desired negative pressure for the second number of times exceeding the second threshold; and
  upon expiration of the third time interval or upon receiving the signal from the switch to activate the source of negative pressure, activate the source of negative pressure to generate the first desired negative pressure under the dressing.

In some embodiments, the controller is further configured to:
  monitor a duty cycle of the source of negative pressure; and
  deactivate the source of negative pressure if the duty cycle exceeds a first duty cycle threshold without the negative pressure reaching the first or second desired negative pressure under the dressing.

In some embodiments, the duty cycle comprises an amount, proportion, or percentage of time the source of negative pressure is active over a period of time.

In some embodiments, the controller is further configured to: calculate a number of duty cycles that exceed the first duty cycle threshold and deactivate the source of negative pressure when the number of duty cycles that exceed the first duty cycle threshold exceeds a second duty cycle threshold.

In some embodiments, the controller is further configured to calculate a number of consecutive duty cycles that exceed the first duty cycle threshold.

In some embodiments, the second duty cycle threshold comprises 30 minutes.

In some embodiments, the controller is further configured: to upon expiration of the third time interval or upon receiving the signal from the switch to active the source of negative pressure, activate the source of negative pressure to generate the first desired negative pressure under the dressing.

In some embodiments, the source of negative pressure comprises a pump.

In some embodiments, the apparatus further comprises: a pressure sensor configured to sense pressure under the dressing and to communicate the sensed pressure to the controller.

In some embodiments, the apparatus further comprises: a one-way valve coupled between an inlet and the source of negative pressure, wherein the inlet is in fluid communication with the dressing.

In some embodiments, the source of negative pressure comprises: a valve configured to connect the port to an external source of negative pressure.

In some embodiments, the controller is further configured to: activate or deactivate the source of negative pressure by operating the valve.

According to a fourth aspect of the present invention there is provided a method of applying negative pressure to a wound, comprising:
  positioning a dressing over the wound to create a substantially fluid impermeable seal over the wound;
  coupling a source of negative pressure to the dressing;
  activating the source of negative pressure to generate a first desired negative pressure under the dressing;
  if, upon an expiration of a first time interval, a negative pressure under the dressing has not reached the first desired negative pressure, deactivating the source of negative pressure for a second time interval; and
  upon expiration of the second time interval, activating the source of negative pressure to generate the first desired negative pressure under the dressing.

In some embodiments, the method further comprises: deactivating the source of negative pressure when the first desired negative pressure has not been generated under the dressing after activating the source of negative pressure for a first number of times exceeding a first threshold.

In some embodiments, the method further comprises: deactivating the source of negative pressure for a third time interval when the first number of times exceeds the first threshold.

In some embodiments, the method further comprises: activating the source of negative pressure to generate the first desired negative pressure under the dressing upon expiration of the third time interval or upon receiving a signal to activate the source of negative pressure from a switch.

In some embodiments, the method further comprises: indicating to a user when the first number of times exceeds the first threshold.

In some embodiments, the method further comprises: stopping the indication upon expiration of the third time interval or receiving a signal to activate the source of negative pressure from the switch.

In some embodiments, the indicating indicates a leak in the seal.

In some embodiments, the method further comprises:
  when the negative pressure under the dressing has reached the first desired negative pressure, deactivating the source of negative pressure and monitoring negative pressure under the dressing; and
  if the negative pressure under the dressing drops below a negative pressure threshold, activating the source of negative pressure to generate a second desired negative pressure under the dressing.

In some embodiments, the first and second desired negative pressure are the same.

In some embodiments, the second desired negative pressure is less than the first desired negative pressure.

In some embodiments, the method further comprises: deactivating the source of negative pressure if the negative pressure under the dressing has reached the second desired negative pressure or if the negative pressure under the dressing has not reached the second desired negative pressure upon expiration of a fourth time interval.

In some embodiments, the method further comprises: if the negative pressure under the dressing has not reached the second desired negative pressure upon expiration of the fourth time interval, activating the source of the negative pressure to generate the first desired negative pressure under the dressing upon expiration of the second time interval.

In some embodiments, the method further comprises: activating the source of the negative pressure to generate the first desired negative pressure under the dressing if the source of negative pressure has been activated to reach the second desired negative pressure for a second number of times less than a second threshold.

In some embodiments, the method further comprises:
  deactivating the source of negative pressure if the source of negative pressure has been activated to reach the second desired negative pressure for the second number of times exceeding the second threshold; and
  upon expiration of the third time interval or upon receiving the signal from the switch to activate the source of negative pressure, activating the source of negative pressure to generate the first desired negative pressure under the dressing.

In some embodiments, the method further comprises:
  monitoring a duty cycle of the source of negative pressure; and
  deactivating the source of negative pressure if the duty cycle exceeds a first duty cycle threshold without the negative pressure reaching the first or second desired negative pressure under the dressing.

In some embodiments, the duty cycle comprises an amount, proportion, or percentage of time the source of negative pressure is active over a period of time.

In some embodiments, the method further comprises: calculating a number of duty cycles that exceed the first duty cycle threshold and deactivating the source of negative pressure when the number of duty cycles that exceed the first duty cycle threshold exceeds a second duty cycle threshold.

In some embodiments, the method further comprises: calculating a number of consecutive duty cycles that exceed the first duty cycle threshold.

In some embodiments, the second duty cycle threshold comprises 30 minutes.

In some embodiments, the method further comprises: upon expiration of the third time interval or upon receiving the signal from the switch to active the source of negative pressure, activating the source of negative pressure to generate the first desired negative pressure under the dressing.

In some embodiments, the source of negative pressure comprises a pump.

In some embodiments, the method further comprises sensing pressure under the dressing.

In some embodiments, the method further comprises: activating or deactivating the source of negative pressure by operating a valve.

Certain embodiments of the present invention provide the advantage that the raising of alarms due to transient leaks into a wound chamber can be avoided, while also reducing the potential for drawing contaminants into a wound site through a leak into the wound chamber.

Certain embodiments of the present invention provide the advantage of extending the useful life of a battery powered source of negative pressure used to provide a desired negative pressure to a wound site.

BRIEF DESCRIPTION OF THE DRAWINGS

Embodiments of the present invention will now be described hereinafter, by way of example only, with reference to the accompanying drawings in which.

In the drawings like reference numerals refer to like parts.

DETAILED DESCRIPTION OF SOME EXEMPLIFYING EMBODIMENTS

Figure 1:
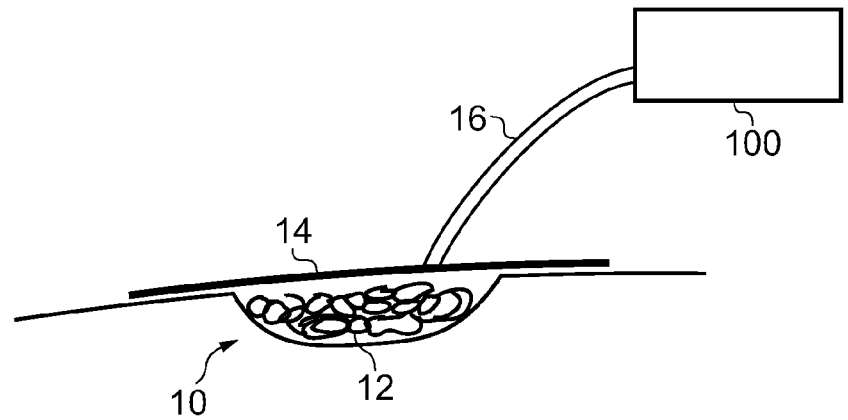
FIG. 1 illustrates an arrangement for applying negative pressure wound therapy to a wound site.

FIG. 1 illustrates an arrangement for applying negative pressure wound therapy to a wound site 10. A packing material 12 is placed within a wound cavity, and then a drape 14 sealed to the surface of the skin around the wound site 10 forming a fluid tight seal around the perimeter of a wound chamber. A source of negative pressure, such as a pressure control apparatus 100 is coupled to the wound cavity via a tube 16. A fluid collection canister (not shown) may be coupled between the pressure control apparatus 100 and the wound chamber to collect any wound exudate drawn from the wound site 10. The use of the packing material 12 is optional, and it may be omitted in certain arrangements as appropriate.

Alternatively, a self contained wound dressing may be used in place of the drape, such a wound dressing absorbs wound exudate within the layers of the dressing removing the need for a separate fluid collection canister.

Further details regarding wound dressings that may be used in combination with the embodiments described herein are found in U.S. application Ser. No. 13/092,042, filed Apr. 21, 2011, the entirety of which is hereby incorporated by reference.

It is envisaged that the negative pressure range for the apparatus in certain embodiments of the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of upto −75 mmHg, upto −80 mmHg or over −80 mmHg can be used. Also aptly a pressure range of below −75 mmHg could be used. Alternatively a pressure range of over −100 mmHg could be used or over −150 mmHg.

Figure 2:
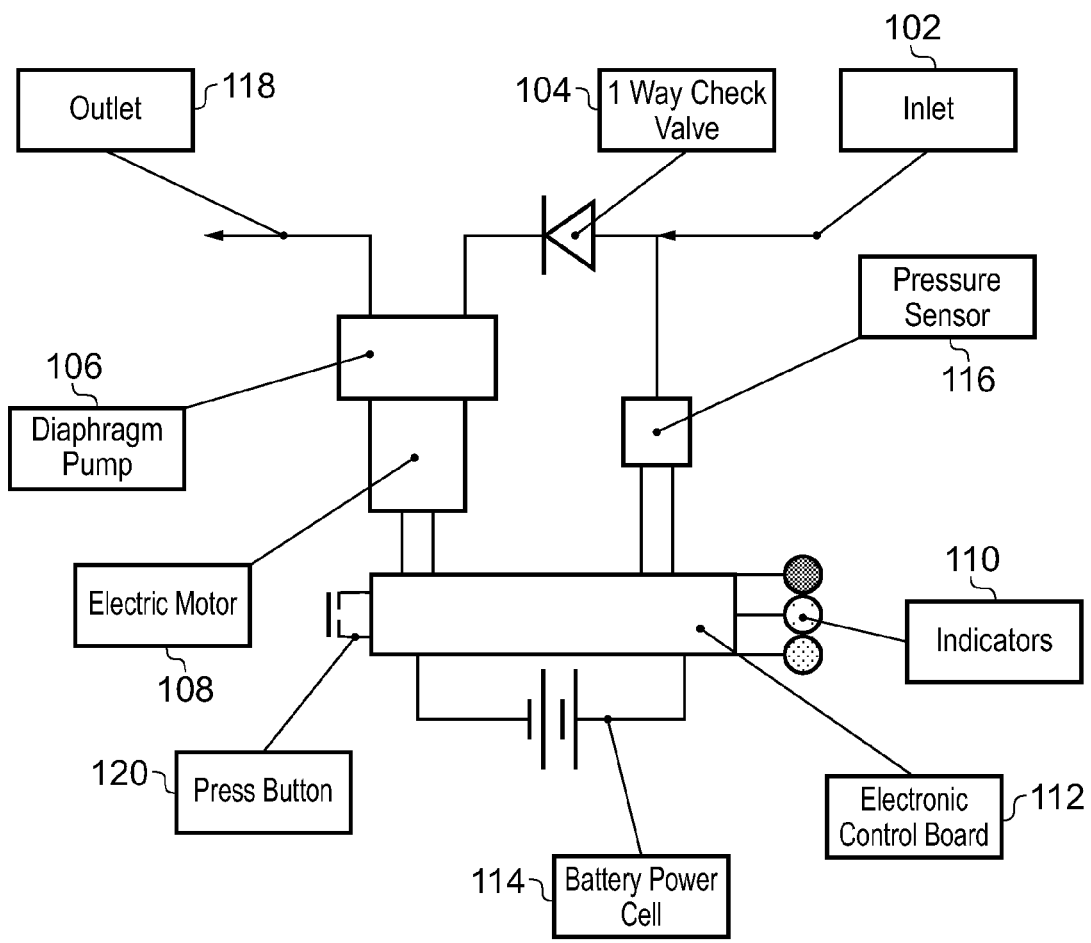
FIG. 2 illustrates a schematic representation of a pressure control apparatus.

FIG. 2 illustrates a schematic representation of a pressure control apparatus 100 according to embodiments of the invention that can be used to apply negative pressure to a wound site 10. The pressure control apparatus includes an inlet 102 coupled to a pressure sensor 116, and also to an inlet of a pump 106 via a one-way check valve 104. The pump is operated by an electric motor 108, which draws power from a battery 114. A controller 112 is coupled to the pressure sensor 116 and provides control signals for controlling the operation of the electric motor 108. Indicators 110 are coupled to the controller 112 to allow audio and/or visual feedback of status signals to a user. An outlet of the pump 106 is coupled to an outlet 118 of the pressure control apparatus. A user can utilise a power button 120 to initiate or terminate operation.

The pump 106 shown is a diaphragm pump which may be highly efficient and capable of providing the required negative pressure. It will be appreciated that other types of pump such as peristaltic pumps, or the like can be used. In some arrangements, the one-way check valve 104 may form part of the pump 106, and may not exist as a separate element of the apparatus.

While the apparatus has been described as being battery powered, it will be understood that the apparatus could alternatively draw electrical power from a mains power supply and the battery power cell removed. In some arrangements, the apparatus may be capable of being powered from either a mains power supply or a rechargeable battery that may be recharged from the mains power supply.

In operation, the inlet 102 is coupled to a wound chamber formed over a wound site 10, for example via the length of tube 16. The electric motor 108 drives the pump 106 under the control of the controller 112 to provide a negative pressure at the inlet 102. The negative pressure can then be communicated to the wound chamber in order to provide a desired negative pressure at the wound site. The check valve 104 maintains the level of negative pressure at the inlet 102 when the pump 106 is not active and helps avoid leaks.

Upon initially connecting the pressure control apparatus 100 to the wound chamber, the pressure at the wound site will be equal to atmospheric pressure, and an initial pump-down must be performed to establish the desired negative pressure at the wound site. This may require the pump 106 to be operated for an extended period of time until the desired negative pressure is achieved.

The pressure at the inlet 102 is indicative of the pressure experienced at the wound site, and this pressure is measured by the pressure sensor 116. The controller 112 receives the pressure value measured at the pressure sensor 116, and once the measured pressure reaches the desired negative pressure, the controller deactivates the pump 106. The controller 112 then continues to monitor the pressure at the pressure sensor.

If during the initial pump-down phase, the controller 112 determines that the desired negative pressure has not been achieved within a certain time (for example 10 minutes or 20 minutes or 30 minutes or 40 minutes or the like), then leaks may be present into the wound chamber, and this condition is signalled via the indicators 110 to show that the wound chamber has not been correctly sealed, or some other error or fault is present.

Once the desired negative pressure has been established, the controller 112 monitors the pressure at the inlet of the pressure control apparatus. From time to time, leaks of fluid may occur into the wound chamber, reducing the level of negative pressure experienced at the wound site, or in other words increasing the absolute pressure at the wound site. The pressure value measured at the pressure sensor 116 and provided to the controller 112 will therefore increase as fluid leaks into the wound chamber. When the measured negative pressure value drops below a certain defined pressure level, the controller 112 will reactivate the pump 106 in order to re-establish the desired negative pressure at the wound site. The desired negative pressure and the defined pressure level at which the controller reactivates the pump provide hysteresis limits between which the pressure should be maintained to apply topical negative pressure to the wound site.

However, if a leak forms that allows fluid, for example air, to leak into the wound chamber with a flow rate greater than the maximum pump capacity 106, it will not be possible for the pressure control apparatus 100 to maintain the desired negative pressure at the wound site. If the pressure control apparatus 100 continued to attempt to re-establish the desired negative pressure in the presence of such a leak, the battery power cell 114 would become depleted.

Furthermore, continued operation of the pump in the presence of a large leak can draw contaminants into the wound site, and lead to excessive drying of the wound site which is undesirable. Therefore, the controller 112 is configured to deactivate the pump 106 if the desired negative pressure is not re-established after operation of the pump 106 for a predetermined period of time. For example sometime between around 30 minutes and 4 hours.

The formation of leaks into the wound chamber may occur due to a range of factors. One common cause of such leaks is movement of a patient being treated with the pressure control apparatus 100. For example, a leak may form when a patient moves from a lying to a sitting position, or during the normal range of movement when walking. Such leaks may be transient, and have been found to regularly reseal as the patient continues to move or returns to their previous position. Thus, there is a risk that the pump 106 may be deactivated due to the detection of a leak that subsequently reseals. However, once the leak reseals, operation of the pressure control apparatus would be able to re-establish the desired negative pressure within the wound chamber.

According to embodiments of the invention, the controller 112 is configured to deactivate the pump 106 after the pump has operated for a certain period of time without the desired level of negative pressure being reached in the wound chamber. That is a timeout event occurs. The controller then waits for a further period of time before a retry attempt is made to re-establish the desired negative pressure at the wound site using the pump 106. If the leak has resealed while the pump has been temporarily deactivated, the retry attempt to re-establish the desired negative pressure will be successful, and operation of the pressure control apparatus 100 can continue as normal. However, if the leak is still present a further timeout event will occur and the pump will be deactivated for the further period of time.

This cycle of deactivating the pump 106 and then attempting to re-establish the desired negative pressure may be repeated a number of times in order to provide an opportunity for any leaks to reseal. However, once a timeout event occurs the negative pressure at the wound site will start to degrade, and therefore there will be a break in the negative pressure wound therapy applied to the wound site. While a short break in therapy may not be a concern, an extended period in which the negative pressure is not applied should preferably be avoided. Furthermore, if a leak path into the wound chamber exists for an extended period of time, the potential for contaminants reaching the wound site increases. Thus, if a number, N, of unsuccessful attempts are made to re-establish the desired negative pressure it can be assumed that the leak is permanent, and not transient, and the controller 112 disables operation of the pressure control apparatus 100 and provides a signal via an audio and/or visual cue to a user that attention is required. This allows a patient or caregiver to arrange for any dressings or drapes to be changed to thereby reform the wound chamber and allow the negative pressure wound therapy to be continued. Aptly N is an integer between 1 and 5 inclusive.

Figure 3:
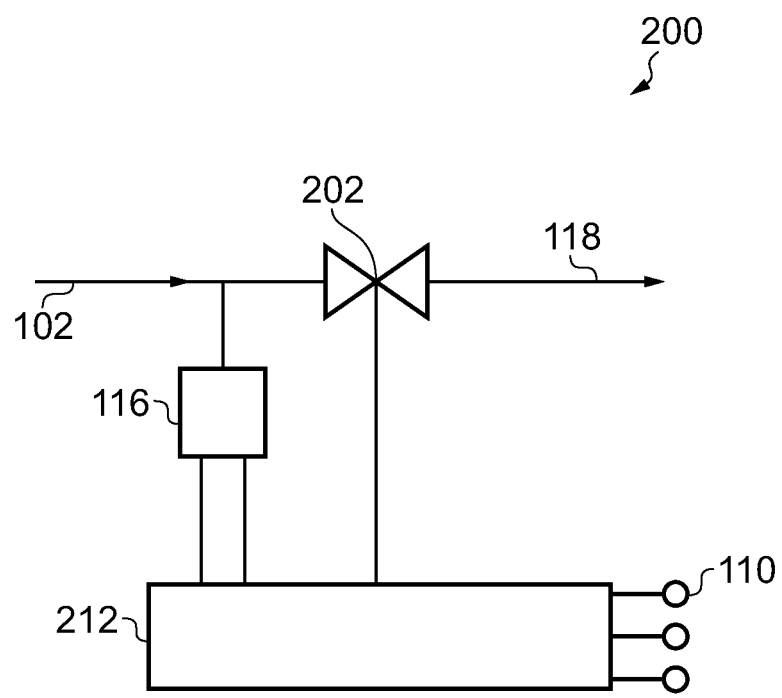
FIG. 3 illustrates a schematic representation of a further pressure control apparatus.

Alternatively, the pump 106 and motor 108 may be omitted, and the negative pressure may be provided via an external source of negative pressure, such as by connection to a vacuum line or vacuum reservoir. FIG. 3 provides a schematic representation of a further pressure control apparatus 200 for use with an external source of negative pressure, and which can be used to provide negative pressure to a wound site 10. Pressure control apparatus 200 includes a controllable valve 202 coupled between an inlet 102 and an outlet 118. The outlet 118 is coupled to the external source of negative pressure. Controller 212 provides control signals to the valve 202 to control the coupling of the external source of negative pressure to the inlet 102, and thereby to the wound chamber. The pressure at the inlet 102 is monitored by a pressure sensor 116, coupled to the inlet, and this monitored pressure is supplied to the controller 212.

The operation of the pressure control apparatus 200 of FIG. 3 is similar to that of the pressure control apparatus 100, except that pressure is controlled by operating the valve 202 to couple the wound chamber to the external source of negative pressure. Controller 112 is able to control the level of negative pressure at the inlet 102 by controlling the valve 202. By monitoring the pressure at the inlet via the pressure sensor 116, the controller 212 can control the valve to provide the desired negative pressure at the wound site.

Unlike the pressure control apparatus of FIG. 2, an extended attempt to provide the desired negative pressure in the presence of a leak will not lead to depletion of a battery power cell. However, longterm it is still undesirable to continue to apply a negative pressure in the presence of a leak due to the possibility of drawing contaminants into the wound chamber, and of drying out the wound site due to the flow of air through the chamber. Thus, the controller 212 of FIG. 3 implements the same control flow as described above with respect to the pressure control apparatus 100. That is, controller 212 is configured to de-couple the inlet 102 from the external source of negative pressure by closing the valve if the desired negative pressure is not established at the wound site within a predetermined period of time. A number of attempts may then be made to re-establish the desired negative pressure in order to provide the opportunity for transient leaks into the wound chamber to reseal.

Thus, the pressure control apparatus of FIGS. 2 and 3 are able to control the application of negative pressure to a wound site, and advantageously reduce the number of alarms due to transient leaks of fluid into the wound chamber. When a leak forms that allows air into the wound chamber at a flow rate above a certain level, the pressure control apparatus is configured to disable the provision of negative pressure to the wound chamber for a predetermined period of time, providing an opportunity for the leak to reseal. Then, if the leak is transient and reseals, the desired negative pressure may then be re-established at a subsequent attempt. This avoids the need to indicate an alarm condition for transient leaks, and also avoids the problem of drawing contaminants and excessive amounts of air into the wound chamber. This also avoids a pump motor being repeatedly energised and de-energised which avoids concerning noise level changes and helps improve pump motor longevity.

Controller 112, 212 may be implemented as a microcontroller, or an application specific integrated circuit, or the like, and may execute instructions to provide the above described control functions. For example, a suitable microcontroller would be one from the STM8L MCU family from ST Microelectronics, for example ST Microelectronics STM8L151G4U6, or one from the MC9S08QE4/8 series from Freescale, such as the Freescale MC9S08QE4CWJ.

The operation of the controller 112 may be described as a finite state machine. The operation of the controller is described below with reference to FIG. 4 which shows a state diagram 300 describing the operation of the controller 112 for the pressure control apparatus shown in FIG. 1.

Figure 5:
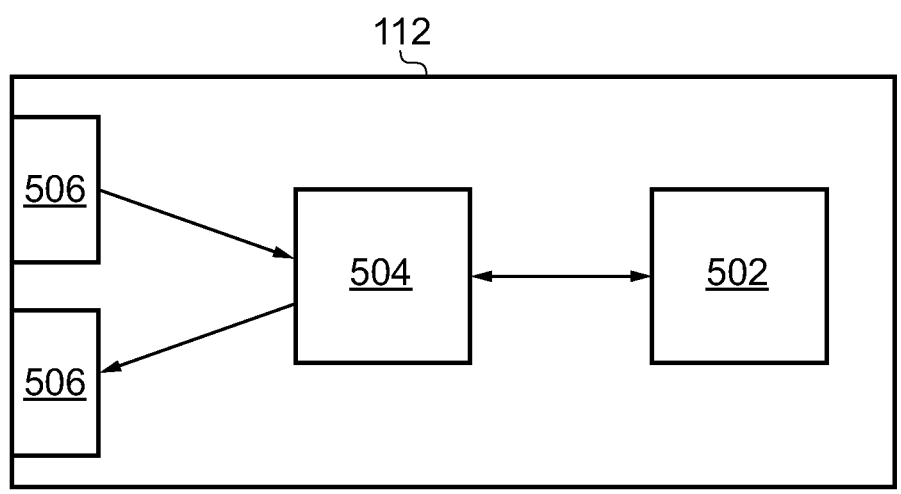
FIG. 5 illustrates a controller.

FIG. 5 illustrates one embodiment of controller 112. The controller comprises a memory 502, which may hold program code for implementing the control functions. The memory is coupled to a microcontroller 504 able to execute the instructions. The microcontroller is coupled to inputs 506 and outputs 508 through which the microcontroller is able to monitor the operation of the system and provide control signals to other parts of the pressure control apparatus.

Referring again to FIG. 4 upon activation 310 of the pressure control apparatus 100 which may occur when an activation strip is pulled for the first time or a user button is pressed or the like, the controller 112 performs a power-on self test (POST) 302 to ensure that the pressure control apparatus is operating correctly. If the power-on self test is failed the pressure control apparatus should not be used Therefore, after a failed POST, the controller transitions to a non-recoverable error state 304 and the error is signalled to the user via indicators 110. If the POST is passed, the controller 112 transitions to an operational state 308 via a standby state, and performs an initial pump down 312 when a user indicates via a button, in which the pump 106 is operated until a desired negative pressure is established in the wound chamber. Alternatively, the controller may wait on a user input before performing the initial pump-down in state 312.

Once the desired negative pressure has been successfully established, the controller transitions to the monitor pressure state 316. However, if after a predetermined period of time the desired pressure has not been established and the initial pump down state 312 is unable to establish the desired negative pressure (indicative of a leak), a timeout occurs. On the first timeout, the controller will transition to a wait state 314, in which the controller waits for a period of time before transitioning back to the initial pump down state 312. Further timeouts may occur from the initial pump-down state 312, and the controller maintains a count of the number of retry attempts made. Once the desired negative pressure has been established, the number of retry attempts may be reset.

If a timeout occurs and the number of retry cycles is greater than a predefined maximum number of retry attempts allowed, the controller transitions to a paused state 306. While in the paused state 306 the controller will transition from the paused state 306 to the initial pump down state 312 in response to a user input, or after a maximum pause time.

In the monitor pressure state 316, the controller monitors the pressure measured at the pressure sensor 116 and, if the pressure drops out of the desired pressure range, the controller transitions to a maintenance pump-down state 318. In the maintenance pump-down state 318, the suction pump is activated either for a predetermined period of time, for example between around 10 and 60 seconds, or until the desired negative pressure is re-established in the wound chamber, whichever occurs sooner.

It is noted that some hysteresis is built into the desired pressure range, such that the pressure value, a minimum desired negative pressure, that triggers a transition from the monitor pressure state 316 to the maintenance pump-down state 318 is lower than the desired negative pressure established in the wound chamber by operation of the pump during the maintenance pump-down state 318. For example, taking the operating pressure ranges discussed above, the desired negative pressure may be −150 mmHg and the minimum desired negative pressure may be −75 mmHg. Alternatively, the controller may act to maintain the pressure within a certain percentage range of the desired negative pressure, for example a 5% hysteresis may be used.

If the desired negative pressure is reached before the suction pump has been operating for the predetermined period of time, the controller transitions back to the monitor pressure state 316.

However, if the pump operates for the predetermined period of time without the desired negative pressure being re-established in the wound chamber, normally due to a leak into the wound chamber, the pressure control apparatus will signal the presence of a leak. If the pressure is within the hysteresis limits, i.e. between the minimum desired negative pressure and the desired negative pressure, this signifies the presence of a high leak, having a flow rate similar to the capacity of the pump. In this situation, the pump continues to operate until the desired negative pressure is re-established, or until the pressure at the wound site is no longer held within the hysteresis limits.

If in the presence of a large leak, the desired negative pressure is restored before a maximum maintenance time is reached, the controller will transition back to the monitor pressure state 316, but will signal the presence of a leak. However, if the suction pump is operated for more than the maximum maintenance time to restore the desired negative pressure, the controller will transition to the paused state 306, while signalling the presence of a leak.

If during the maintenance pump-down state 318, the pressure in the wound chamber is not maintained within the hysteresis limits, a catastrophic leak has occurred, and the controller transitions to the wait state 314.

In some embodiments, if after a predetermined period of time, the desired pressure has not been established and the maintenance pump down state 318 is unable to establish the desired negative pressure before the maximum maintenance time is reached, a timeout occurs. On the first timeout, the controller will transition to the wait state 314, in which the controller waits for a period of time before transitioning back to the initial pump down state 312. Further timeouts may occur from the maintenance pump-down state 318, and the controller maintains a count of the number of retry attempts made. Once the desired negative pressure has been established in the maintenance pump down state 318, the number of retry attempts may be reset. If a timeout occurs and the number of retry attempts is greater than a predefined maximum number of retry attempts allowed, the controller transitions to the paused state 306, as described above.

Figure 4:
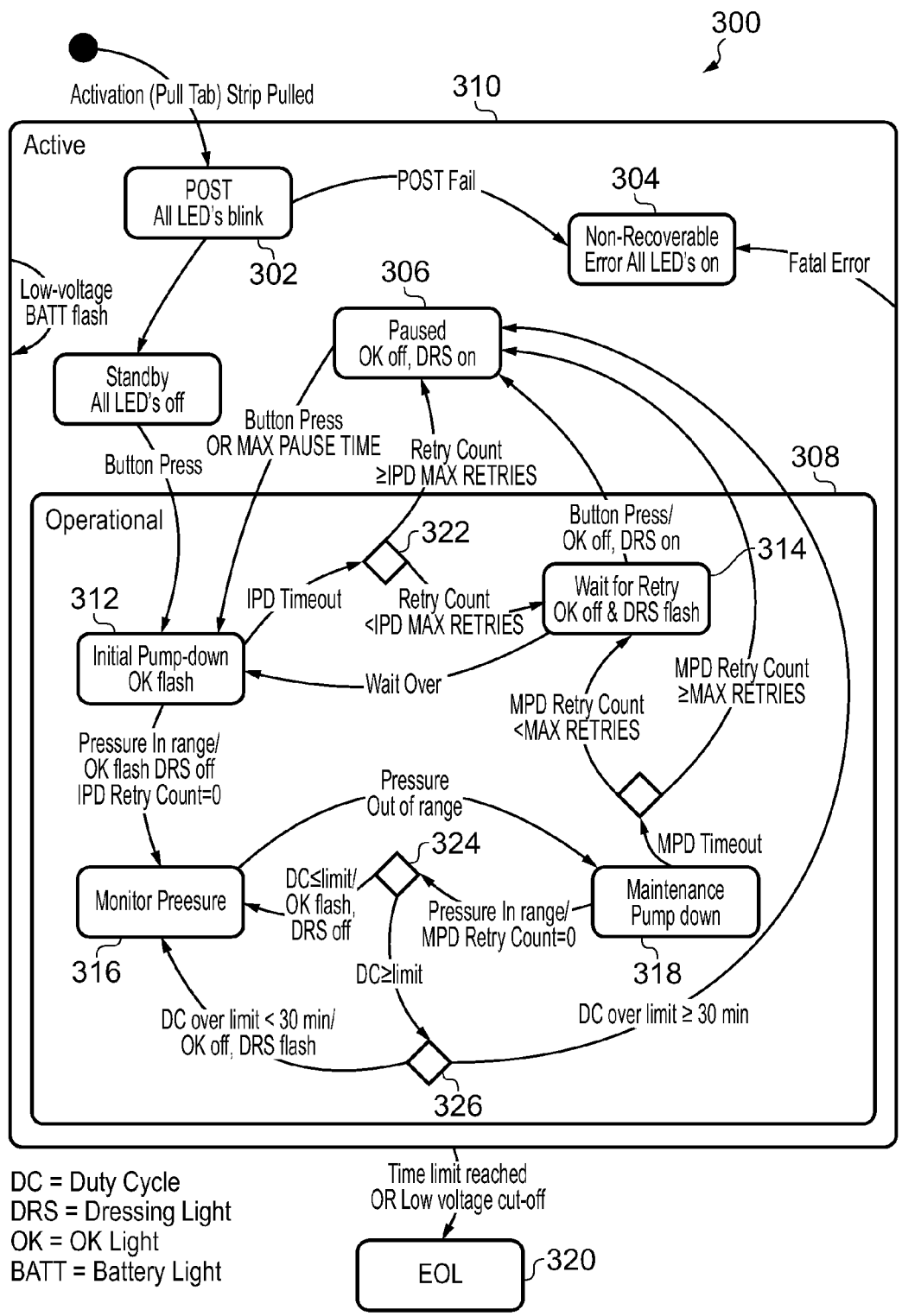
FIG. 4 illustrates a state diagram of a controller.

Thus, if the leak is such that it is over a prescribed limit and the pump duty cycle (DC) as defined, in some embodiments, as pump on time divided by pump off time is over a predetermined limit then the pump shall continue to operate within the hysteresis limits for a particular time duration. For example, around 30 minutes as shown in FIG. 4. Thus, in the monitor pressure loop if the duty cycle is less than a predetermined limit then all is okay. If the duty cycle is greater than a particular limit but less than a time out time the pump continues to run for up to 30 minutes. If DC is greater than time out then a paused state 306 is entered.

At any time while in the operational state 308, the controller may be placed in the pause state 306 in response to a user input. Once the battery voltage reaches a low voltage cut off level or the lifetime of the pressure control apparatus has been reached, the controller de-activates the pressure control apparatus and an End of Life state is reached.

The controller 212 described with respect of the pressure control apparatus 200 of FIG. 3 operates in a similar manner as described above except that the initial pump-down and maintenance pump-down states are replaced with valve activation states in which the inlet 102 is coupled to the external source of negative pressure connected to the outlet 118 via controllable valve element 202.

Alternatively, the POST state 302 may be omitted.

The pressure control apparatus may be configured to be re-useable and be provided with a switch to allow the apparatus to be turned on and off as required. Such a re-usable apparatus may include rechargeable power cells, and may provide a low power indication in order to allow the power cells to be replaced/recharged.

In a disposable single use pressure control apparatus, activation may be provided by pulling an activation strip and it may not be possible to deactivate the apparatus once activated until the apparatus is to be discarded.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method of treating a wound implemented by a controller of a negative pressure wound therapy device, the method comprising:
   in response to receiving a request from a user interface of the negative pressure wound therapy device to initiate negative pressure wound therapy, activating a source of negative pressure to attempt to generate a desired negative pressure at the wound;
   if the desired negative pressure has not been reached after a first period of time, deactivating the source of negative pressure for a second period of time; and
   subsequently attempting to generate the desired negative pressure at the wound.

2. The method as claimed in claim 1, further comprising:
   if the desired negative pressure has not been reached after a third period of time, deactivating the source of negative pressure for the second period of time, and subsequently attempting to generate the desired negative pressure at the wound.

3. The method as claimed in claim 2, further comprising:
   when the desired negative pressure has not been reached after the third period of time, deactivating the source of negative pressure for the second period of time and subsequently attempting to generate the desired negative pressure at the wound.

4. The method as claimed in claim 2, further comprising:
   deactivating the source of negative pressure when the desired negative pressure has not been reached after a threshold number of attempts.

5. The method as claimed in claim 4, further comprising:
   providing an indication when the desired negative pressure has not been reached after the threshold number of attempts.

6. The method as claimed in claim 1, wherein the source of negative pressure comprises a pump, and activating the source of negative pressure comprises activating the pump.

7. The method as claimed in claim 6, wherein deactivating the source of negative pressure comprises deactivating the pump.

8. The method as claimed in claim 1, wherein:
   the source of negative pressure comprises a valve configured to be coupled to an external source of negative pressure and activating the source of negative pressure comprises opening the valve.

9. The method as claimed in claim 8, wherein deactivating the source of negative pressure comprises closing the valve.

10. The method as claimed in claim 1, further comprising:
    monitoring a duty cycle of the source of negative pressure; and
    deactivating the source of negative pressure if the duty cycle satisfies a duty cycle threshold without successfully reaching the desired negative pressure at the wound.

11. The method as claimed in claim 10, wherein the duty cycle comprises an amount of time the source of negative pressure is active over a time period.

12. The method as claimed in claim 1, further comprising:
    monitoring a plurality of duty cycles of the source of negative pressure;
    calculate a number of duty cycles from the plurality of duty cycles that satisfy a first duty cycle threshold; and
    deactivating the source of negative pressure if the number of duty cycles satisfies a second duty cycle threshold.

13. The method as claimed in claim 1, further comprising:
    monitoring negative pressure at the wound; and
    if the monitored negative pressure is below a threshold negative pressure, attempting to generate the desired negative pressure at the wound.

14. The method as claimed in claim 13, wherein:
    the threshold negative pressure is more positive than the desired negative pressure.

15. The method as claimed in claim 1, further comprising:
    maintaining the desired negative pressure at the wound after the desired negative pressure at the wound has been reached.

16. The method as claimed in claim 15 wherein maintaining comprises:
    monitoring a level of negative pressure at the wound; and
    when it has been determined that the level of negative pressure at the wound is more positive that a pressure threshold, activating the source of negative pressure to attempt to generate the desired negative pressure at the wound.

17. The method as claimed in claim 16, further comprising:
    deactivating the source of negative pressure when desired negative pressure has been reached.

18. The method as claimed in claim 17, further comprising:
    deactivating the source of negative pressure when desired negative pressure has not been reached after a third period of time.

19. The method as claimed in claim 1, further comprising:
    providing an indication if the desired negative pressure has not been reached after the first period of time.

20. The method as claimed in claim 1, further comprising:
    providing an indication when the desired negative pressure at the wound has been reached.

* * * * *